United States Patent [19]
Pabst

[11] Patent Number: 5,632,000
[45] Date of Patent: May 20, 1997

[54] DEVICE FOR OPTIMIZING THE SPEED CONTROL BEHAVIOR OF A SUBFRACTIONAL HORSEPOWER MOTOR

[75] Inventor: Josef Pabst, Heddesheim, Germany

[73] Assignee: Siemens Aktiengesellschaft, Munich, Germany

[21] Appl. No.: 416,222

[22] Filed: Apr. 4, 1995

[30] Foreign Application Priority Data

Apr. 11, 1994 [DE] Germany ............ 44 12 413.9

[51] Int. Cl.$^6$ .................................. H02P 5/00
[52] U.S. Cl. .................. 388/806; 388/811; 388/901; 388/903
[58] Field of Search .................. 388/800–830, 388/432, 594, 854, 901, 903; 318/439, 779, 729, 778, 811

[56] References Cited

U.S. PATENT DOCUMENTS

| | | | |
|---|---|---|---|
| 3,617,844 | 11/1971 | Grygera | 318/308 |
| 3,688,167 | 8/1972 | Ivey et al. | 318/45 |
| 3,716,772 | 2/1973 | Larson | 318/332 |
| 4,152,632 | 5/1979 | Peterson | 318/317 |
| 4,468,603 | 8/1984 | Vander Meer et al. | 318/779 |
| 4,656,403 | 4/1987 | Treffer | 318/341 |
| 4,866,356 | 9/1989 | Altendorf | 388/811 |
| 4,891,764 | 1/1990 | McIntosh | 318/432 |
| 5,350,988 | 9/1994 | Le | 318/618 |

FOREIGN PATENT DOCUMENTS

3221146C2  12/1983  Germany.

*Primary Examiner*—Paul Ip
*Attorney, Agent, or Firm*—Hill, Steadman & Simpson

[57] ABSTRACT

A device for the optimizing of the speed control of an electric subfractional horsepower motor for dental instruments is provided wherein it is possible to operate the motor in any desired speed range. The device contains a first module for regulating the speed by voltage measurement, a second module for regulating the speed by current-load compensation, and means for deciding which of the two modules and in what proportion they assume speed regulation of the motor.

12 Claims, 3 Drawing Sheets

DEVICE FOR OPTIMIZING THE SPEED CONTROL BEHAVIOR OF A SUBFRACTIONAL HORSEPOWER MOTOR

BACKGROUND OF THE INVENTION

1. Field of the Invention

The present invention is directed to a device for optimizing the speed control of a subfractional horsepower motor such as those typically used in dental instruments.

2. Description of the Prior Art

Two conventional control devices of this type are known in the art and disclosed in DE 32 21 146. In one of these designs, the regulation of the speed is accomplished through compensation of the internal voltage drop of the motor. The motor current is measured dependent on the motor load. Given a reduction in speed as a result of a higher load, a higher motor current is measured. Conversely, the speed increases with a reduction in load, and consequently a lower motor current is measured. The measured difference in motor current is fed to a controller that adjusts the speed to the desired value. An advantage of this type of motor regulation is extremely quiet operation of the motor even into its upper speed range. One disadvantage however, is that the motor provides relatively low torque, especially in its lowest speed range. The increases in current are too slight to compensate by measurement; in contrast thereto, the collector losses are felt to a relatively large degree.

In the second conventional control device, the speed is calculated by measuring the voltage with the motor switched off. One advantage of this design is that it provides extremely good torque for the motor, even in its lowest speed range. The regulation can compensate the collector losses well, and as a result speeds having high torque can be regulated down to zero. One disadvantage of this control method is that rough running that can lead to vibration may occur under certain circumstances in the upper speed range. The reason for this is that system-deactivation of the motor is necessary for the voltage measurement.

One object of the present invention is thus to provide a device that makes it possible to operate a subfractional horsepower motor of the type primarily used for dental equipment in such a way that it can be optimally controlled in every desired speed range. The device will provide optimum speed control even with different load values in both the lower as well as the upper speed range.

SUMMARY OF THE INVENTION

The present invention is based on a system which embodies the two aforementioned control devices and which processes each measurement. The device which is set forth in greater detail below can, preferably automatically, undertake a sliding transition from the voltage control into the current-load control and vice versa on the basis of predetermined motor data. The decision as to when the user must switch between two types of regulation is thus eliminated. The motor data required for the input, i.e. the switching speed on the one hand and the maximum speed at which the motor is to be operated, can either be permanently prescribed or can be set by the user.

DESCRIPTION OF THE PREFERRED EMBODIMENTS

Figure 1:
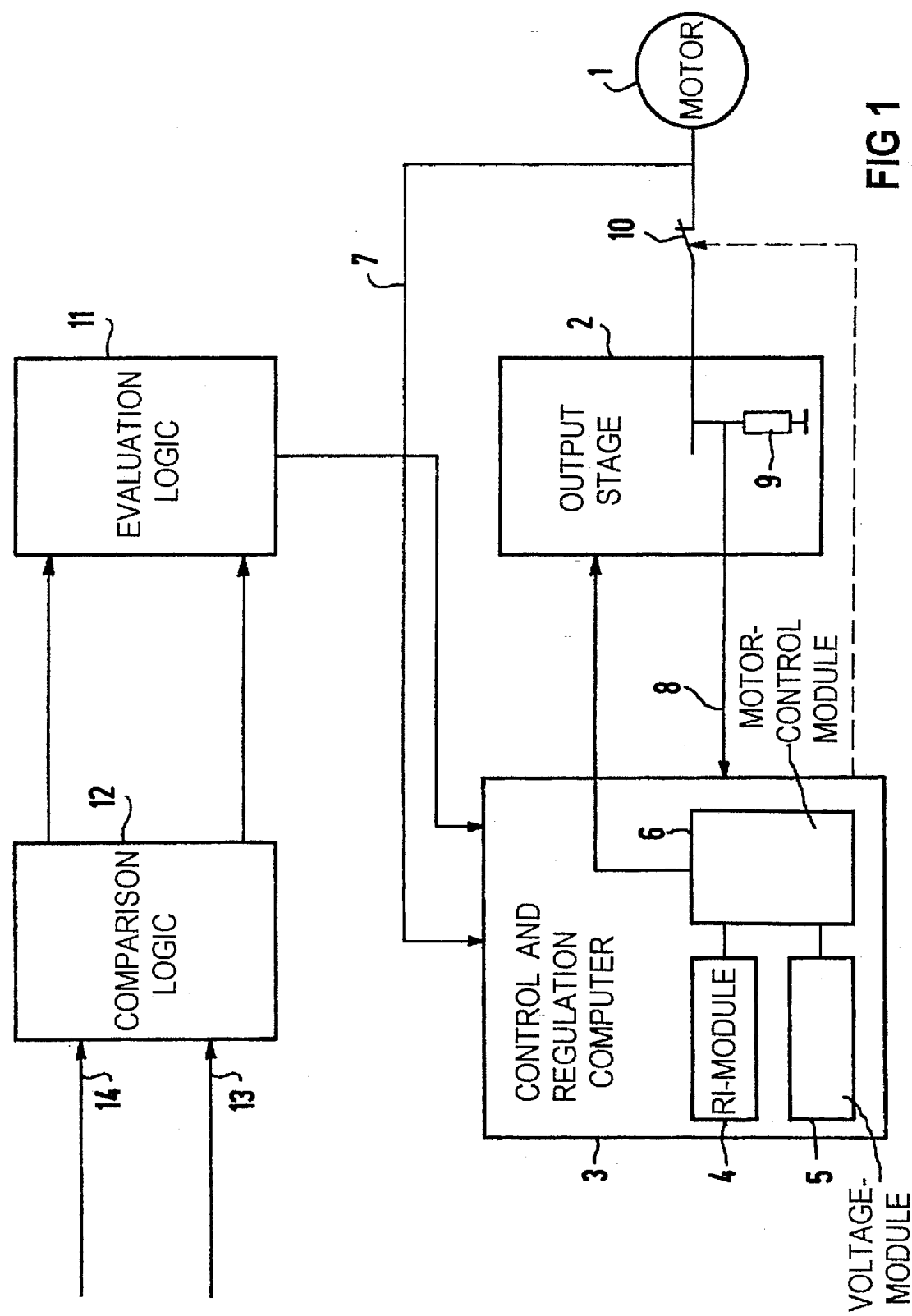
FIG. 1 is a circuit block diagram of a first embodiment of the present invention.

A first exemplary embodiment of the present invention is set forth in FIG. 1. An electric motor 1 is driven by an output stage 2 that converts data from a control and regulation computer 3 into motor speed and motor torque. The computer 3 contains a current-load module 4 and voltage module 5. The current-load module 4 processes the incoming motor data according to the initially described current-load compensation method. The voltage module 5 processes the incoming motor data according to the voltage measurement. The motor control module 6 is connected to the motor output stage 2 and drives the output stage according to either the current-load control method or according to the voltage control method.

The motor speed data required for voltage measurement is input into the computer via the line 7. Information for the current load compensation, which is obtained in a known way via a resistor 9, is input into the computer 3 via the line 8. Corresponding control information is also forwarded by the computer 3 to a current shut-off circuit 10 required for the voltage measurement.

An evaluation logic circuit 11 decides whether voltage or current load control is to be used. The information required for the decision is supplied by comparison logic 12 into which information about the desired, maximum speed is input via input 13. Information about the selected switching speed U at which the change is to be made from voltage control to current load control is input via an additional input 14. Comparison logic 12 decides whether the current speed, i.e. the actual speed, is higher or lower than the switching speed U and forwards the result to evaluation logic 11. The input of the switching speed U can be input by the operator at a panel or in some other manner. The same is true of the desired, maximum speed at which the motor is to be operated.

Figure 2:
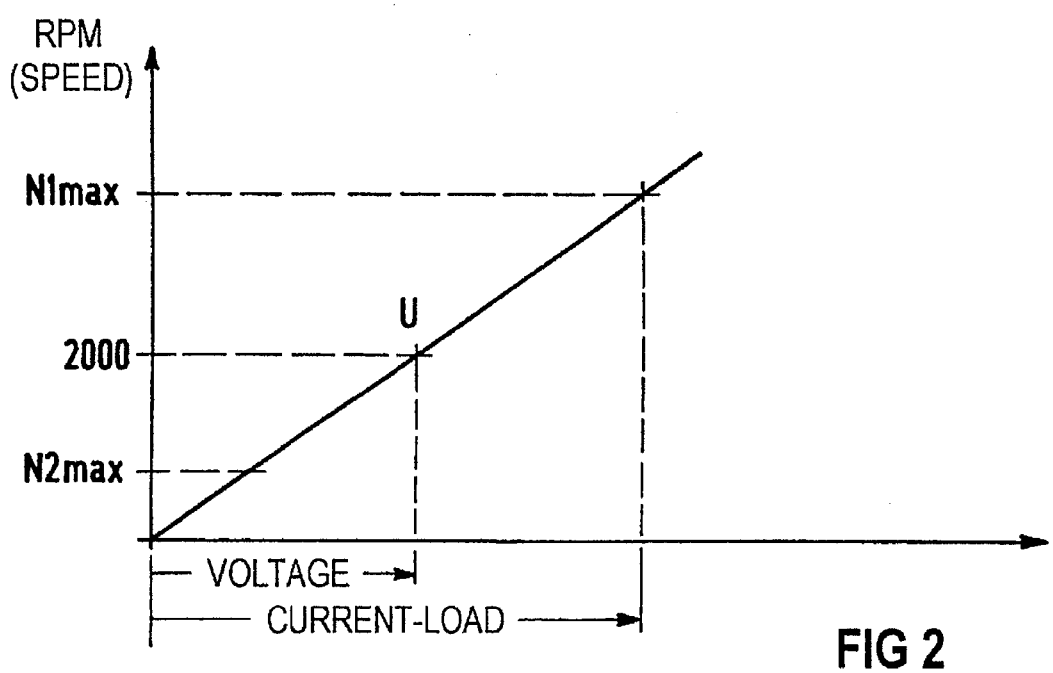
FIG. 2 is a graph illustrating operation of the present invention.

The switching event is set forth with reference to the diagram of FIG. 2. The switching speed U at which a switch is undertaken from voltage to current-load control and vice versa can be defined by the user. For example, this switching value should be at a rated value of 2,000 rpm. When the maximum speed N1max is above the switching speed U, for example at 40,000 rpm, then regulation ensues according to current-load compensation. When, in contrast, the maximum speed N2max lies below this value, for example at 800 rpm, then speed regulation is accomplished only with voltage measurement. The switching speed U can be advantageously set by the individual user. It is desirable, however, to permanently set this at the time of installation of a dental apparatus wherein the subfractional horsepower motor is utilized. The maximum desired speed can be automatically called in during the treatment or can also be manually input. When the desired speed is above the switching speed U, the current-load compensation is used for the entire, selected speed range. When, in contrast, procedures are to be carried out that require a speed in the lower speed range, then the user will select a maximum speed below the switching speed U. The voltage control is automatically activated for this selection, this resulting therein that the motor 1 outputs a relatively high torque even in the lower speed range.

Figure 3:
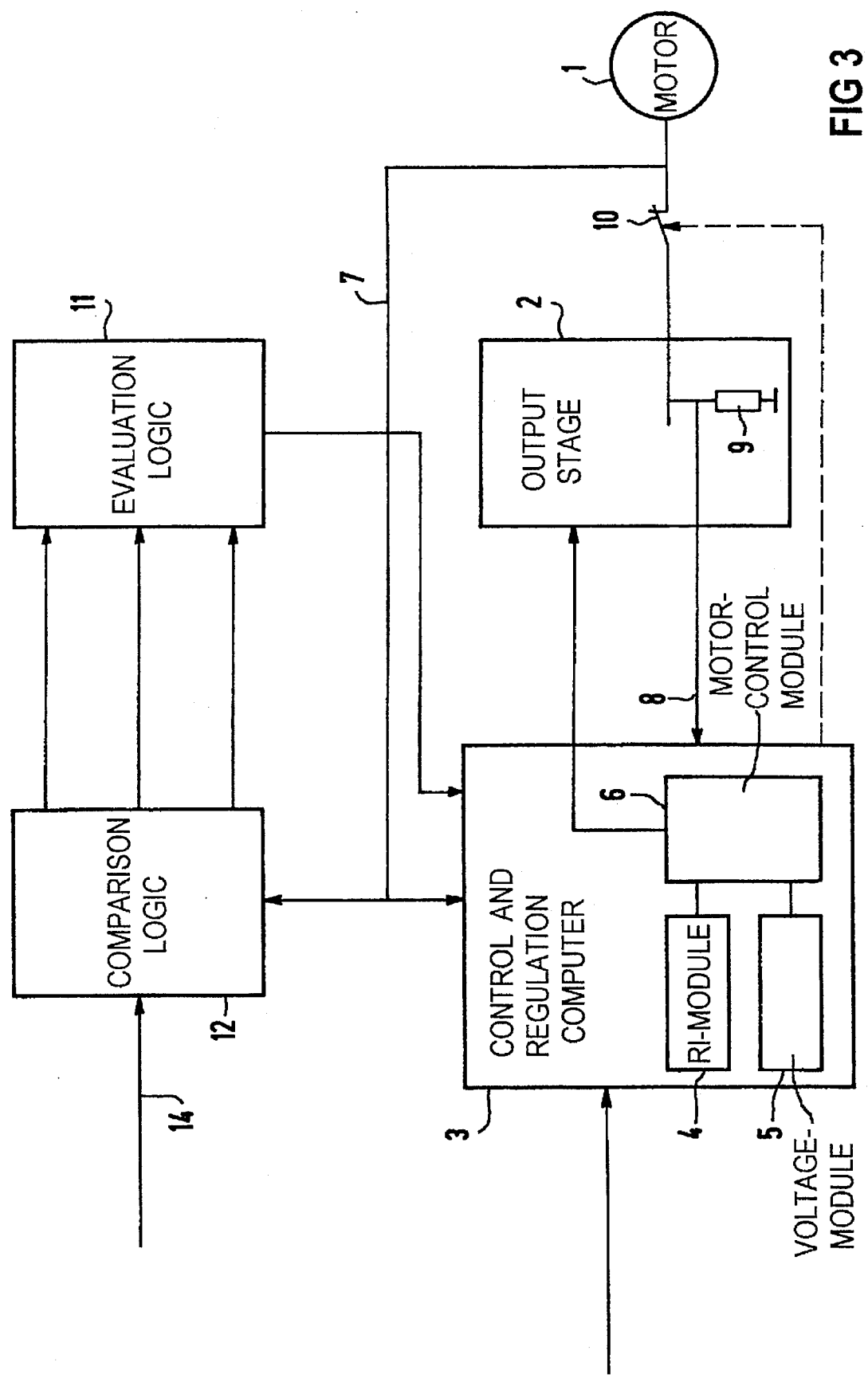
FIG. 3 is a block diagram of a second embodiment of the present invention.

FIG. 3 shows an embodiment wherein the adaptation to the two types of control or regulation ensues automatically.

Figure 4:
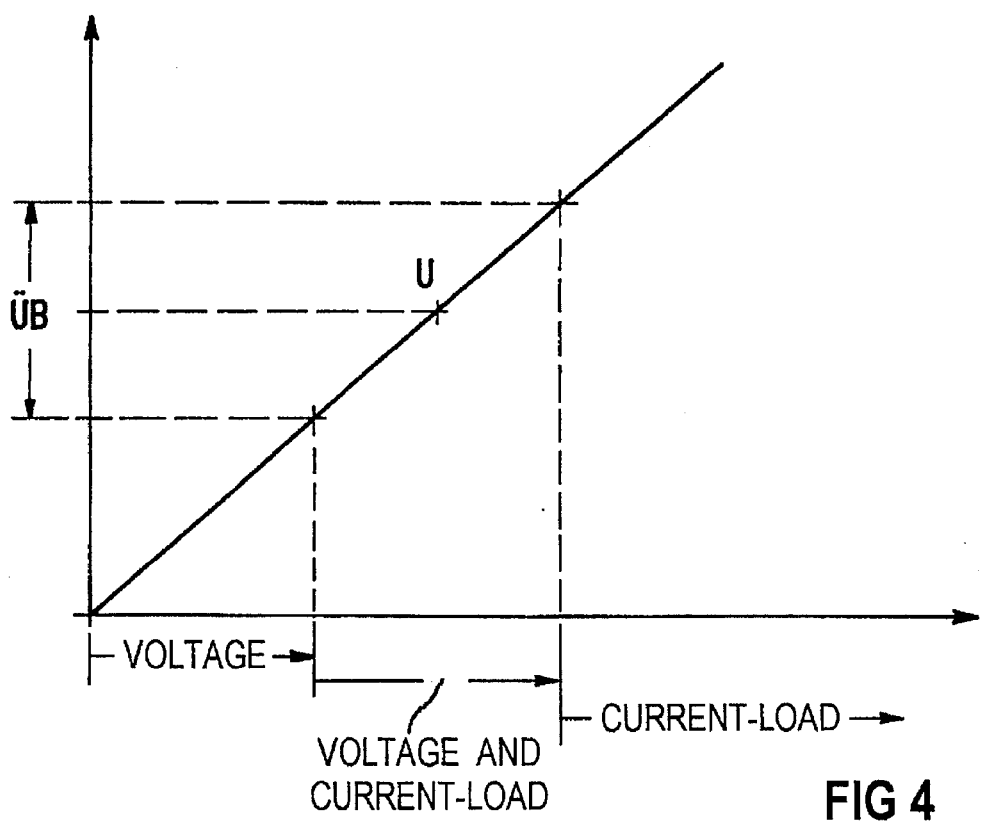
FIG. 4 is a graph illustrating operation of the present invention.

In contrast to the above-described exemplary embodiment, it is not the switching speed U but a switching range that is input via input 14 of comparison logic 12. The comparison logic 12 compares whether the current speed that is likewise input into the comparison logic 12 via the line 7 is above, below or within the switching range. When the current motor speed lies in the switching range, the evaluation logic 11 decides how many switching parts or, respectively, regulating parts should take effect. This information is supplied to the computer 3 that then selects either the current load module 4 or the voltage module 5 or corresponding portions of the two modules for control characteristics. Viewing the diagram of FIG. 4, it may be seen that all the more current load control parts must be activated the closer the current motor speed comes to the switching speed U. At the same time the voltage influences are slowly eliminated. When the speed in turn drops, the proportions shift in the opposite direction. When the electronics is in the current load range, the speed is only rarely measured, so that the motor exhibits extremely quiet running. In contrast, when the speed again approaches the transition range, the voltage regulation starts to become active. Below the transition range, only the voltage regulation takes effect. The interruption of the motor current for the speed measurement required in this lower speed range, however is unnoticeable in this speed range.

The present invention is subject to many variations modifications and changes in detail. It is intended that all matter described throughout the specification and shown in the accompanying drawings be considered illustrative only. Accordingly, it is intended that the invention be limited only by the spirit and scope of the appended claims.

I claim as my invention:

1. A speed control device for a subfractional horsepower motor comprising a voltage speed regulator for regulating a speed of said motor by voltage control of said motor, said voltage speed regulator generating a first regulation signal; a current-load regulator for regulating said speed of said motor by current-load compensation, said current-load generator generating a second regulation signal, and means for selectively controlling the motor using said first regulation signal or using said second regulation signal dependent on motor data having inputs connected to the first and second regulation signals.

2. The speed control device of claim 1, wherein the means for selectively controlling the motor comprises a comparison logic circuit which receives motor data that correspond to a switching speed at which a transition is made from operation under control of the voltage regulator to operation under control of the current-load regulator and which compares an actual speed to the switching speed to obtain a comparison result, and an evaluation logic circuit supplied with said comparison result which selects control of said motor using said first or second regulation signal depending on said comparison result.

3. The speed control device of claim 2, wherein said motor data comprise a maximum speed quantity.

4. The speed control device of claim 3, wherein the maximum speed is freely selected by a motor user.

5. The speed control device of claim 4, wherein a first speed range is defined and wherein the means for selectively controlling the motor selects regulating the motor speed by current-load compensation when an actual speed is within the first speed range.

6. The speed control device of claim 1, wherein said motor data comprise a control characteristic for switching between the current-logic regulator and the voltage regulator stored in a memory and further comprising a computer which determines whether the first or second regulation signal will control the motor based on said control characteristic.

7. A method of controlling a subfractional horsepower motor system comprising a voltage speed regulator and a current-load regulator, said method comprising the steps of:

measuring an actual speed of the motor;

comparing the measured actual speed with a selected switching speed to obtain a comparison result; and selecting either the current-load regulator or the voltage regulator for controlling said motor dependent on said comparison result.

8. A speed control device for a subfractional horsepower motor comprising:

a voltage speed regulator for regulating a speed of said motor by voltage control of said motor, said voltage speed regulator generating a first regulation signal;

a current-load regulator for regulating said speed of said motor by current-load compensation, said current-load generator generating a second regulation signal, and means for selectively controlling the motor using said first regulation signal or using said second regulation signal dependent on motor data having inputs connected to the first and second regulation signals;

wherein the means for selectively controlling the motor comprises a comparison logic circuit which receives motor data that correspond to a switching speed at which a transition is made from operation under control of the voltage regulator to operation under control of the current-load regulator and which compares an actual speed to the switching speed to obtain a comparison result, and an evaluation logic circuit supplied with said comparison result which selects control of said motor using said first or second regulation signal depending on said comparison result.

9. The speed control device of claim 8, wherein said motor data comprise a maximum speed quantity.

10. The speed control device of claim 9, wherein the maximum speed is freely selected by a motor user.

11. The speed control device of claim 10, wherein a first speed range is defined and wherein the means for selectively controlling the motor selects regulating the motor speed by current-load compensation when an actual speed is within the first speed range.

12. The speed control device of claim 8, wherein said motor data comprise a control characteristic for switching between the current-logic regulator and the voltage regulator stored in a memory and further comprising a computer which determines whether the first or second regulation signal will control the motor based on said control characteristic.

* * * * *